United States Patent
Hartmann-Bax et al.

(10) Patent No.: US 9,302,095 B2
(45) Date of Patent: Apr. 5, 2016

(54) RELEASABLE CONTACT CONNECTION ARRANGEMENT FOR ELECTRODES ON AN ELECTROMEDICAL DEVICE

(71) Applicant: BIOTRONIK SE & Co. KG, Berlin (DE)

(72) Inventors: Kathy Hartmann-Bax, Nuthe-Urstromtal (DE); Annett Ortscheid, Falkensee (DE)

(73) Assignee: BIOTRONIK SE & Co. KG, Berlin (DE)

( * ) Notice: Subject to any disclaimer, the term of this patent is extended or adjusted under 35 U.S.C. 154(b) by 90 days.

(21) Appl. No.: 14/244,360

(22) Filed: Apr. 3, 2014

(65) Prior Publication Data

US 2014/0316498 A1 Oct. 23, 2014

Related U.S. Application Data

(60) Provisional application No. 61/813,187, filed on Apr. 18, 2013.

(51) Int. Cl.
- *A61N 1/00* (2006.01)
- *A61N 1/05* (2006.01)
- *A61N 1/375* (2006.01)
- *H01R 13/52* (2006.01)

(52) U.S. Cl.
CPC ............ *A61N 1/0551* (2013.01); *A61N 1/3752* (2013.01); *H01R 13/5224* (2013.01); *H01R 2201/12* (2013.01)

(58) Field of Classification Search
USPC .......................................................... 607/36
See application file for complete search history.

(56) References Cited

U.S. PATENT DOCUMENTS

| | | |
|---|---|---|
| 5,489,225 A | 2/1996 | Julian |
| 2002/0161413 A1 | 10/2002 | Knapp |
| 2003/0018364 A1 | 1/2003 | Belden et al. |
| 2005/0222634 A1 | 10/2005 | Flickinger et al. |
| 2010/0029127 A1 | 2/2010 | Sjostedt |
| 2010/0217107 A1* | 8/2010 | Hill ........................ A61N 1/057 600/377 |

OTHER PUBLICATIONS

European Search Report and Notes to the European Search Report on European Patent Application No. EP 14 16 3712, dated Jul. 21, 2014 (7 pages).

* cited by examiner

*Primary Examiner* — Nicole F Lavert
(74) *Attorney, Agent, or Firm* — Buchanan Ingersoll & Rooney PC

(57) ABSTRACT

A releasable contact connection arrangement for electrodes on an electromedical device, in particular for electrodes of active implants, such as neurostimulator devices, includes a contact end, which is provided on the electrode and comprises at least one electrical contact, a device-side connector head on the electromedical device, a connector opening on the connector head for anchoring the contact end of the electrode so as to produce an electrical contact connection and releasable mechanical fixing, and an anti-kink device at the exit of the contact end from the connector opening, wherein the anti-kink device includes a flexible anti-kink sleeve sitting on the contact end of the electrode before the at least one electrical contact, said anti-kink sleeve being slid via its fixing end facing the connector head into a receiving recess that is enlarged compared to the connector opening and being fastened therein.

20 Claims, 3 Drawing Sheets

RELEASABLE CONTACT CONNECTION ARRANGEMENT FOR ELECTRODES ON AN ELECTROMEDICAL DEVICE

CROSS-REFERENCE TO RELATED APPLICATIONS

This patent application claims the benefit of U.S. Provisional Patent Application No. 61/813,187, filed on Apr. 18, 2013, which is hereby incorporated by reference in its entirety.

TECHNICAL FIELD

The present invention relates to a releasable contact connection arrangement for electrode leads on an electromedical device and, in particular, for electrode leads of implantable neurostimulator devices, having the features specified in the preamble of claim 1.

BACKGROUND

Releasable contact connection arrangements of the above-mentioned type normally comprise a contact end, which is provided on the electrode lead and comprises at least one electrical contact, a device-side connector head on the electromedical device, a connector opening on the connector head for anchoring the contact end of the electrode lead so as to produce an electrical contact connection and a releasable mechanical fixing, and an anti-kink device at the exit of the contact end from the connector opening.

It is noted with regard to the background of the invention that releasable contact connection arrangements of this type, particularly when used with electrode leads for neurostimulators, require what is known as a "360° anti-kink device" at the transition from the device-side connector to the electrode lead, since the electrode leads of such electromedical devices can be deflected laterally practically in all spatial directions from the longitudinal axis of the connector end.

The anti-kink device that is necessary in this regard is known in principle from the prior art in accordance with public prior use by the Applicant herein. It consists of a connection piece integrally formed on the connector head of the electromedical device around the discharge of the connector opening in combination with an anti-kink bushing displaceable on the electrode. A tube piece protruding from the connector head is also known and fulfills the purpose of an anti-kink measure.

These known solutions have a disadvantage in that they protrude from the surface of the connector head, said surface being smooth per se, which does not allow the surfaces of the connector head to be reworked, for example, deburred and/or polished. The reason for this lies primarily in the fact that these connector heads for forming these anti-kink devices are generally formed completely from potting resin, which hinders surface finishing in order to meet high quality demands.

Based on at least the above-mentioned problem(s) of the prior art, an object of the present invention is to create an anti-kink device on a generic releasable contact connection arrangement, said anti-kink device allowing independent reworking of the connector head of the electromedical device with high anti-kink action.

The present invention is directed toward overcoming one or more of the above-identified problems.

SUMMARY

At least one object of the present invention is achieved by the features specified in the independent claim(s). The anti-kink device therefore comprises a flexible, that is to say pliable, anti-kink sleeve sitting on the contact end of the electrode lead before the at least one electrical contact, said anti-kink sleeve being slid via its fixing end facing the connector head into a receiving recess that is enlarged compared to the connector opening and being fastened therein.

A basic concept of the present invention is therefore the spatial separation of the anti-kink device from the connector head, which has to comprise a corresponding receiving recess for the fixing end of the anti-kink sleeve. Since this recess does not form a protrusion on the surface of the connector head, but forms a depression or indentation, which is in any case closed by the fixing end of the anti-kink sleeve when the electrode lead is attached, the surface can be reworked at the connector head without difficulty and the connector head itself may consist of a material selected on the basis of its surface quality. The use of a potting resin for the production of the connector head is possible without difficulty due to the omitted bushing or tube protrusion on the connector head. An effective 360° anti-kink device is also formed by the anti-kink sleeve at the transition to the connector head, and is also resistant to relatively large forces and muscular movements, as may occur precisely in the environment of active implants, such as, for example, neurostimulator devices.

Preferred developments of the subject matter of the present invention are specified in the dependent claims. The head area of the anti-kink sleeve pointing in the longitudinal axial direction may thus cooperate in the form of a stop face with the base area of the enlarged receiving receptacle. The anti-kink sleeve thus simultaneously forms the stop for the insertion of the contact end of the electrode lead into the connector opening of the device. The insertion depth of the connector end is thus fixed.

In accordance with a preferred development, the anti-kink sleeve is provided with a marking or other visual or physical indication at a distance from its head area, said distance corresponding to the depth of the receiving recess. A possibility for visually or physically checking the positioning of the electrode lead in the attached state is thus provided.

In one form, the marking is preferably formed by an annular groove in the anti-kink sleeve, said annular groove running peripherally in the peripheral direction. The positioning of the contact end of the electrode lead in the connector opening can thus also be ascertained "blindly" with the aid of the sense of touch.

The possible truncated conical shape, tapering in the direction of the electrode lead, of the anti-kink sleeve in accordance with a further preferred embodiment assists the gentle handling of the electrode as said electrode is deflected from the axial direction of the connector opening in the connector head.

In accordance with a development that is uncomplicated in terms of production and advantageous in terms of material, the anti-kink sleeve is produced from a solid, injection molded, flexible biocompatible elastomer, preferably in combination with at least one support element made of ceramic, metal or plastic.

For the arrangement of the anti-kink sleeve on the electrode lead, two basic alternatives are possible. On the one hand, a stationary fixing of the anti-kink sleeve on the contact end of the electrode lead is possible. The position of the anti-kink sleeve can thus be assigned in a clean and exact manner relative to the contact end and, therefore, also relative to the connector opening, and therefore the stop function and positioning check by means of the insertion of the anti-kink sleeve into the recess in the receiving opening are possible in a particularly reliable manner.

In accordance with a further preferred embodiment, the intended molding of the anti-kink sleeve directly onto the contact end of the electrode can be produced in a simple manner.

In accordance with variants of the above, the anti-kink sleeve can also be welded on or adhesively bonded on, wherein a biocompatible adhesive is to be preferred in the latter case.

As an alternative to the fixed connection between the anti-kink sleeve and electrode lead, the anti-kink sleeve may also be mounted displaceably on the electrode lead.

In accordance with a further preferred embodiment, the longitudinally axially running sleeve opening of the anti-kink sleeve can be sealed with respect to the contact end of the electrode by at least one seal element. Axial and radial sealing functions can thus be performed by the anti-kink sleeve. Conventional configurations, such as, for example, a ring seal, a crowned sealing face, and/or a sealing lip can be provided for the formation of the seal element. If the anti-kink sleeve is fabricated from a flexible material, such as, for example, silicone, seal elements of this type can be formed without difficulty on the anti-kink sleeve.

This flexible formation is also incidentally advantageous in conjunction with the displaceability of the anti-kink sleeve on the electrode. Due to a radially inwardly flexible specification, in particular of the material of the anti-kink sleeve, a user can press said sleeve together between his thumb and index finger, whereby a temporary fixing of the sleeve on the electrode line is produced, which can be released again before letting go of said sleeve.

A further preferred sealing measure may consist in providing a peripheral sealing shoulder on the outer face of the fixing end of the anti-kink sleeve, said sealing shoulder cooperating with the inner wall of the receiving recess and therefore hermetically sealing the recess.

Furthermore, for further improved fixing of the anti-kink sleeve in the recess, a fastening element may be provided, in particular in the form of a detent mechanism between two components, and may be formed by a fastening shoulder arranged peripherally on the fixing end and by a corresponding annular groove in the inner wall of the recess. In the assembled position of the anti-kink sleeve, this fastening shoulder then latches into the annular groove and provides a reliable hold.

Still further, in accordance with a further preferred development of the contact connection arrangement, the discharge of the connector opening and/or the head area of the anti-kink sleeve is/are provided with a peripheral chamfer. This chamfer causes a self-centering of the anti-kink sleeve as it is inserted into the recess in the connector head. The use of the electromedical device is therefore facilitated.

Additional features, aspects, objects, advantages, and possible applications of the present invention will become apparent from a study of the exemplary embodiments and examples described below, in combination with the figures, and the appended claims.

DESCRIPTION OF THE DRAWINGS

Further features, details and advantages of the present invention will emerge from the following description of an exemplary embodiment(s) with reference to the accompanying drawings, in which.

DETAILED DESCRIPTION

Figure 1:
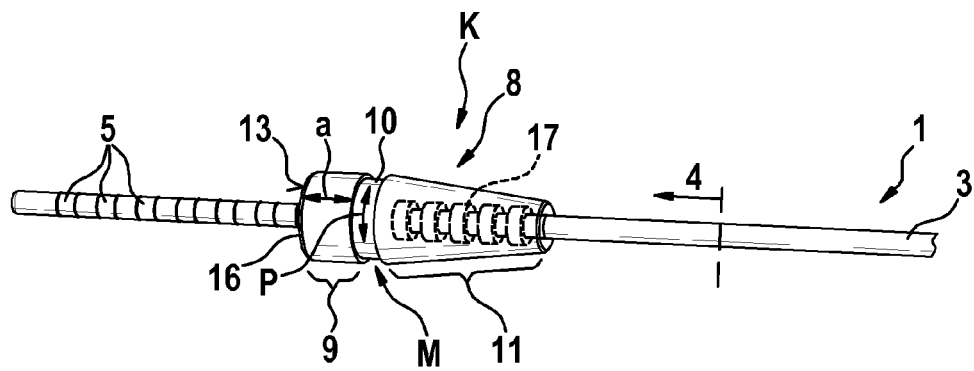
FIG. 1 shows a perspective partial view of an electrode lead in the region of its contact end with anti-kink sleeve.
Figure 2:
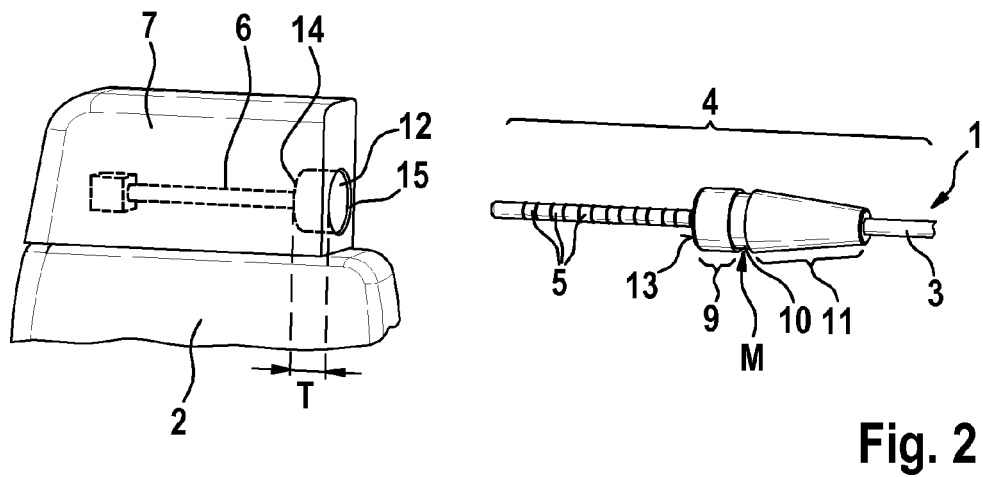
FIG. 2 shows a perspective partial view of an electrode lead, similarly to FIG. 1, with an electromedical device before the insertion of the contact end of the electrode lead into the connector head of the device.
Figure 3:
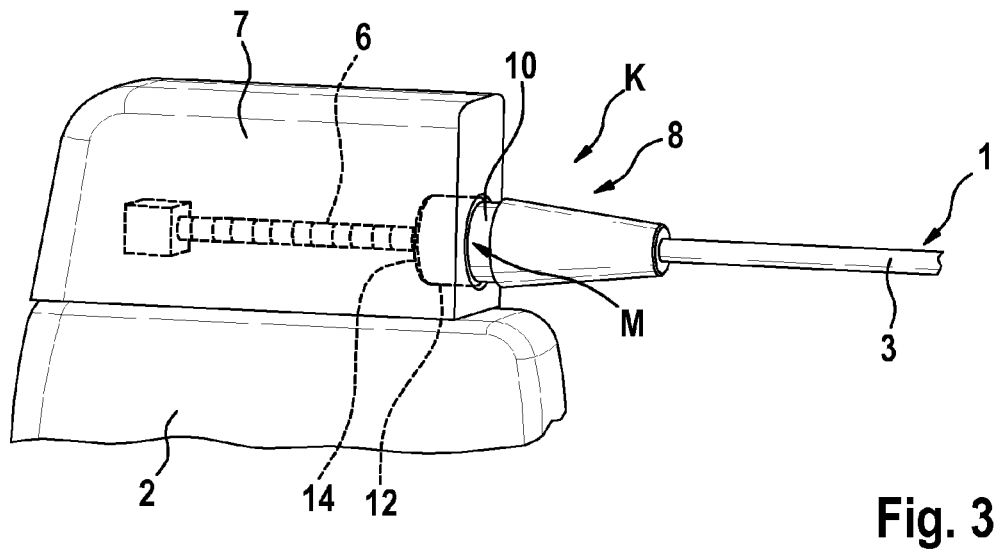
FIG. 3 shows a perspective partial illustration of electrode lead and device with connector head in the contacted state.
Figure 4:
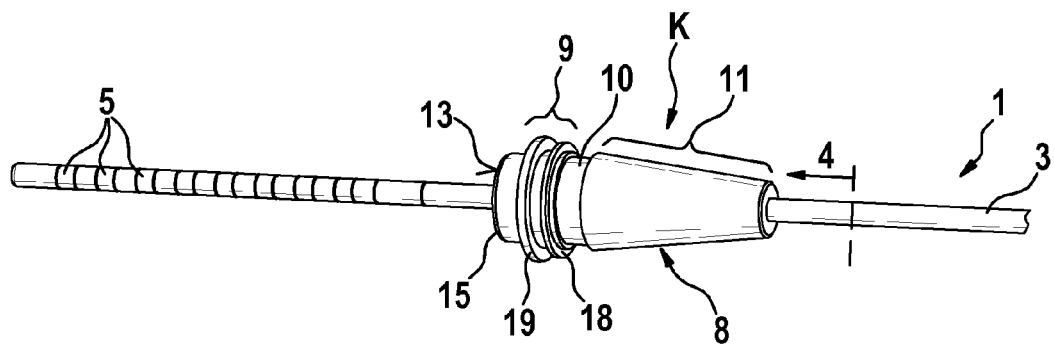
FIG. 4 shows a perspective partial view of an electrode lead in the region of its contact end with anti-kink sleeve in a second embodiment.

As can be seen from FIGS. 1 to 3, an electrode lead 1 for example of an implantable (neurostimulator) device 2 (see FIGS. 2 and 3) comprises an insulating tubular electrode lead body 3 with a contact end 4, on which a plurality of electrical contacts 5 are arranged. These electrical contacts cooperate with corresponding mating contacts (not illustrated) in the connector head 7 of the device 2, which are connected accordingly to the electronic control unit of the device 2.

To protect the electrode lead 1 against dynamic movements, bending moments, and the like, an anti-kink device, denoted on the whole by K, is provided at the exit of the contact end 4 from the connector opening 6, which is formed in the shown exemplary embodiment by an anti-kink sleeve 8. The anti-kink sleeve 8 consists of a flexible biocompatible elastomer and is molded directly onto the lead body 3. The sleeve body is divided here into a fixing end 9 facing the contacts 5 on the contact end, an annular groove 10 running peripherally in the peripheral direction P, and a truncated, conically tapering bushing region 11. As a mating part, the cylindrical fixing end 9 of the anti-kink sleeve 8 has an inner cylindrical receiving recess 12, which forms the connector opening 6 and is oriented coaxially therewith.

The distance between the annular groove 10 and the head area 13 of the fixing end 9 corresponds to the depth T of the receiving recess 12. If the contact end 4 of the electrode lead 1 is inserted into the connector opening 6, the head area 13 cooperates in the form of a stop with the base 14 of the recess 12, such that the annular groove 10 then functions as a marking M, which can be detected visually and by means of touch, for the correct positioning of the contact end 4 of the electrode lead 1 in the connector opening 6, as can be seen clearly with reference to FIG. 3. The annular groove 10 may also be formed in a raised manner as an annular shoulder. A visual marking in the form of a print is also conceivable, as well as any individual or combination of visual and physical markings.

Additionally, it is clear from FIGS. 1 and 2 that both the head area 13 at its edge and also the discharge of the connector opening 6 are provided with a chamfer 15 and 16, respectively, by means of which the insertion of the fixing end 9 of the anti-kink sleeve 8 into the recess 12 is facilitated and these two components are self-centered relative to one another.

As is illustrated in a dashed manner in FIG. 1, an insert 17 made of, for example, plastic, metal, elastomer and/or ceramic, may be embedded in the anti-kink sleeve to reinforce the sleeve.

The embodiment shown in FIGS. 4 to 7 of the electrode lead 1 corresponds in terms of the basic embodiment to the variant according to FIGS. 1 to 3. In this regard, matching components are provided with identical reference numbers/letters and do not require any renewed explanation. To avoid repetitions, reference is made to the corresponding description of FIGS. 1 to 3.

Differences of the embodiment according to FIGS. 4 to 7 lie in the additional attachment of the seal and fastening elements on the fixing end 9 of the anti-kink sleeve 8 and also in the receiving recess 12 of the connector head 7. As is clear in this regard, a peripheral shoulder seal 18 is provided in the region of the fixing end 9 as a seal element and cooperates with the inner diameter of the recess 12, which is slightly smaller compared to the outer diameter of the shoulder seal 18, and ensures a corresponding seal when the anti-kink sleeve 8 is inserted into the recess 12.

A fastening shoulder 19 that is larger in outer diameter and cross section is integrally formed before the shoulder seal 18 in the direction toward the contact end 4 of the electrode and is formed as an annular protrusion running peripherally in the peripheral direction. This fastening shoulder 19 cooperates with a corresponding annular groove 20 in the inner wall of the recess 12. After insertion of the anti-kink sleeve 8 into the recess 12, the fastening shoulder 19 latches into the annular groove 20, whereby a particularly stable anchoring of the anti-kink sleeve 8 in the connector head 7 of the device 2 is achieved.

Figure 5:
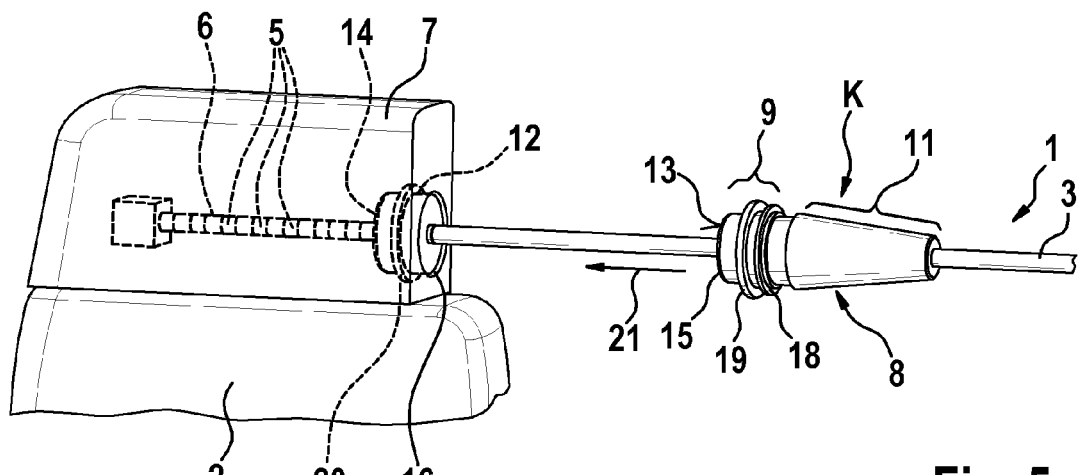
FIG. 5 shows a perspective partial view of an electrode lead, similarly to FIG. 4, with an electromedical device before the insertion of the contact end of the electrode lead into the connector head of the device.
Figure 6:
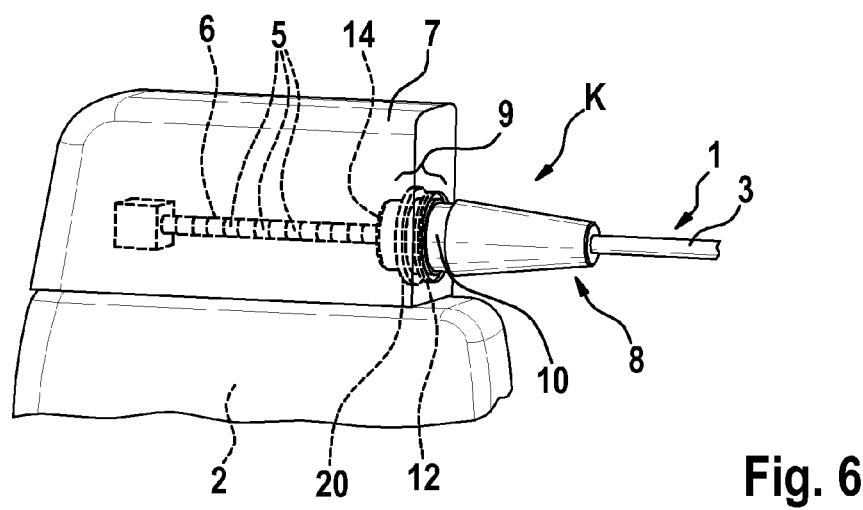
FIG. 6 shows a perspective illustration of the electrode lead according to FIGS. 4 and 5 and of an electromedical device with the connector head in the contacted state.

As is clear from a combination of FIGS. 5 and 6, a version of the anti-kink sleeve 8 displaceable on the electrode body 3 is shown herein. Specifically, in FIG. 5, the electrode lead 1 is already introduced via its contact end 4 into the connector opening 6 of the connector head 7 in the end position. The anti-kink sleeve 8 is still located at a considerable distance before the connector head 7.

In order to bring the electrode lead 1 into this position shown in FIG. 5, the user can clamp the anti-kink sleeve 8 between his thumb and index finger as a result of the flexible design of the anti-kink sleeve 8, whereby said sleeve 8 is temporarily fixed on the electrode lead body 3. The anti-kink sleeve 8 thus acts as a sort of thickened grip for the electrode lead body 3, which can therefore be introduced comfortably into the connector opening 6. By letting go of the anti-kink sleeve 8, said sleeve 8 relaxes again and can be slid on the electrode lead body 3 in the direction of the recess 12, as indicated by the arrow 21, and can be brought into the end assembly position shown in FIG. 6.

Figure 7:
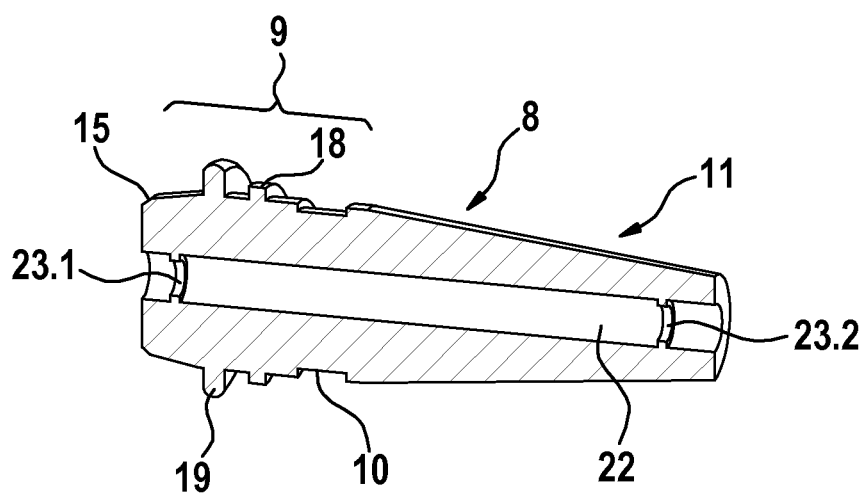
FIG. 7 shows a perspective longitudinal axial section of the anti-kink sleeve used with the electrodes lead according to FIGS. 4 to 6.

In order to seal the sleeve opening 22, which runs longitudinally axially and is visible in FIG. 7, with respect to the lead body 3, said sleeve opening comprises an inwardly projecting sealing lip 23.1, 23.2 before each of the two ends, said sealing lips being hermetically supported tightly against the outer face of the lead body 3.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A releasable contact connection arrangement for electrode leads on an electromedical device, in particular for electrode leads of active implants, such as neurostimulator devices, the contact connection arrangement comprising:
   a contact end, which is provided on the electrode lead and comprises at least one electrical contact,
   a device side connector head on the electromedical device,
   a connector opening on the connector head for anchoring the contact end of the electrode lead so as to produce an electrical contact connection and releasable mechanical fixing, and
   an anti-kink device at an exit of the contact end from the connector opening,
   wherein the anti-kink device comprises a flexible anti-kink sleeve sitting on the contact end of the electrode lead before the at least one electrical contact, said anti-kink sleeve having a fixing end and is capable of being slid via the fixing end into a receiving recess, when the fixing end is facing the connector head, and being fastened therein, wherein the recess is enlarged compared to the connector opening.

2. The contact connection arrangement as claimed in claim 1, wherein a head area of the fixing end of the anti-kink sleeve pointing in a longitudinal axial direction cooperates in a form of a stop face with a base area of the enlarged receiving recess.

3. The contact connection arrangement as claimed in claim 2, wherein the anti-kink sleeve is provided with a marking at a distance from its head area, said distance corresponding to a depth of the receiving recess.

4. The contact connection arrangement as claimed in claim 3, wherein the marking is formed by an annular groove, annular shoulder, visual marking, or imprint in or on the anti-kink sleeve, running peripherally in a peripheral direction.

5. The contact connection arrangement as claimed in claim 1, wherein the anti-kink sleeve other than in a region of the fixing end and/or other than in a region of the annular groove has a truncated conical shape, tapering in a direction of the electrode lead.

6. The contact connection arrangement as claimed in claim 1, wherein the anti-kink sleeve other than in a region of the fixing end has a cylindrical shape with recesses for enhancing flexibility.

7. The contact connection arrangement as claimed in claim 1, wherein the anti-kink sleeve comprises a solid, injection molded, flexible biocompatible elastomer in combination with at least one support element made of ceramic, metal or plastic.

8. The contact connection arrangement as claimed in claim 1, wherein the anti-kink sleeve is fixed in a stationary manner on the contact end of the electrode lead.

9. The contact connection arrangement as claimed in claim 7, wherein the anti-kink sleeve is molded directly onto the contact end of the electrode lead.

10. The contact connection arrangement as claimed in claim 8, wherein the anti-kink sleeve is welded on the contact end of the electrode lead or is adhesively bonded thereon with the aid of a biocompatible adhesive.

11. The contact connection arrangement as claimed in claim 1, wherein the anti-kink sleeve is mounted displaceably on the contact end of the electrode lead.

12. The contact connection arrangement as claimed in claim 11, wherein the anti-kink sleeve comprises a longitudinally axially running sleeve opening, which is sealed by at least one seal element.

13. The contact connection arrangement as claimed in claim 11, wherein the seal element is formed by a ring seal, crowned seal face or a sealing lip.

14. The contact connection arrangement as claimed in claim 1, wherein the fixing end of the anti-kink sleeve is provided with a seal element cooperating with the receiving recess, and is provided with a circumferential sealing shoulder.

15. The contact connection arrangement as claimed in claim 1, wherein the fixing end of the anti-kink sleeve is provided with a fastening element cooperating with the receiving recess, and is provided with a fastening shoulder for latching with an annular groove in the receiving recess.

16. The contact connection arrangement as claimed in claim 1, wherein an orifice of the connector opening and/or a head area of the anti-kink sleeve is/are provided with a centering aid comprising a peripheral chamfer.

17. The contact connection arrangement as claimed in claim 1, wherein an insert for reinforcement is embedded in the anti-kink sleeve.

18. A releasable contact connection arrangement for an electrode lead, comprising:
   a sleeve body capable of being attached to a lead body of the electrode lead, the sleeve body having a fixing end with a head area and a base, the fixing end having an inner receiving recess forming a connector opening, the sleeve body having an annular groove running peripherally in a peripheral direction so that a distance exists between the annular groove and the head area of the fixing end; and,
   a connector head attached to an electromedical device, the connector head having mating contacts configured to cooperate with a portion of the electrode lead;
   wherein when the sleeve body is attached to the electrode lead and the electrical lead is inserted into the connector opening, the head area cooperates as a stop when engaging the base such that the annular groove functions as a marking.

19. A releasable contact connection arrangement for an electrode lead, comprising:
   an electrode lead having a lead body and a contact end, the contact end having a plurality of electrical contacts arranged thereon;
   a sleeve body capable of being attached to the lead body, the sleeve body having a fixing end with a head area and a base facing the plurality of contacts when attached to the lead body, the fixing end having an inner receiving recess forming a connector opening, the sleeve body having an annular groove running peripherally in a peripheral direction so that a distance exists between the annular groove and the head area of the fixing end; and,
   a connector head attached to an electromedical device, the connector head having mating contacts configured to cooperate with the plurality of electrical contacts;
   wherein when the contact end is inserted into the connector opening, a spatial separation exists between the sleeve body and the connector head.

20. The releasable contact connection arrangement as claimed in claim 19, wherein the sleeve body comprises flexible material so as to facilitate pressing the sleeve body together to temporarily fix the sleeve body to the electrode body for displaceably attaching the sleeve body to the electrode body.

* * * * *